United States Patent [19]

Andree et al.

[11] Patent Number: 5,068,394
[45] Date of Patent: Nov. 26, 1991

[54] HERBICIDAL (HETERO)ARYLOXYNAPHTHALENE DERIVATIVES AND INTERMEDIATES THEREFOR

[75] Inventors: Roland Andree, Langenfeld; Michael Haug, Bergisch-Gladbach; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 424,035

[22] Filed: Oct. 19, 1989

[30] Foreign Application Priority Data

Nov. 4, 1988 [DE] Fed. Rep. of Germany ....... 3837464

[51] Int. Cl.$^5$ .............................................. C07C 69/76
[52] U.S. Cl. ...................... 560/56; 562/466; 562/840; 562/849; 564/180; 558/188; 558/197; 558/214; 558/427; 560/10; 546/24; 546/302; 546/312; 546/342; 71/108; 71/105
[58] Field of Search ................. 560/56, 466, 480, 489; 71/108, 105

[56] References Cited

U.S. PATENT DOCUMENTS 2,547,123 4/1951 Horeau et al. ........................ 560/56

Primary Examiner—Paul J. Killos
Attorney, Agent, or Firm—Sprung, Horn, Kramer & Woods

[57] ABSTRACT

Herbicidal (hetero)aryloxynaphthalene derivatives of the formula

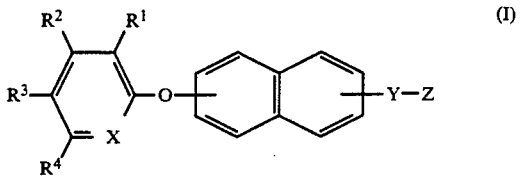

(I)

in which
X is N or —C—$R^5$,
$R^1$, $R^2$, $R^4$ and $R^5$ are hydrogen or halogen or $R^1$ may be cyano or trifluoromethyl,
$R^3$ is halogen, trifluoromethyl, trifluoromethoxy, trifluoromethylthio or trifluoromethylsulphonyl,
Y is optionally halogen-substituted alkanediyl or alkenediyl, and
Z is CN or —CC—Z′, where
Z′ is halogen, hydroxyl, amine, alkoxy, or the like.

Intermediates of the formula

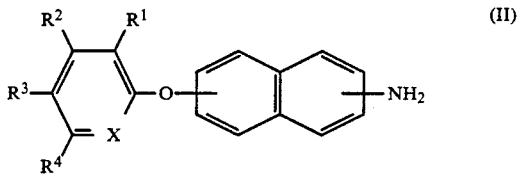

(II)

are also new.

14 Claims, No Drawings

HERBICIDAL (HETERO)ARYLOXYNAPHTHALENE DERIVATIVES AND INTERMEDIATES THEREFOR

The invention relates to new (hetero)aryloxynaphthalene derivatives, to processes and new (hetero)aryloxynaphthylamines for their preparation, and to their use as herbicides.

It is already known that certain dioxy-benzene derivatives, such as, for example, methyl α-(4-(2,4-dichlorophenoxy)-phenoxy)-propionate (diclofop-methyl) are herbicidally active (cf. DE-OS (German Published Specification) 2,223,894). However, the action of these known compounds against weeds, as well as their tolerance by crop plants, are not always satisfactory.

New (hetero)aryloxynaphthalene derivatives of the general formula (I)

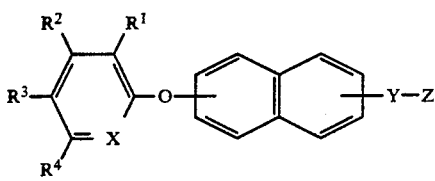

in which
$R^1$ represents hydrogen, halogen, cyano or trifluoromethyl,
$R^2$ represents hydrogen or halogen,
$R^3$ represents halogen, trifluoromethyl, trifluoromethoxy, trifluoromethylthio or trifluoromethylsulphonyl,
$R^4$ represents hydrogen or halogen,
X represents nitrogen or the C—$R^5$ group, where
  $R^5$ represents hydrogen or halogen,
Y represents in each case optionally branched and/or optionally halogen-substituted alkanediyl or alkenediyl, in each case having at least 2 carbon atoms, and
Z represents cyano or the —CO—$Z^1$ group, where
  $Z^1$ represents halogen, hydroxyl, amino, alkylamino, alkenylamino, alkinylamino, arylamino, aralkylamino, alkoxycarbonylalkylamino, cyanoamino, dialkylamino, dialkenylamino, alkylsulphonylamino, arylsulphonylamino, hydroxyamino, alkoxyamino, hydrazino, alkylsulphonylhydrazino, arylsulphonylhydrazino, alkylthio, arylthio, aralkylthio or alkoxycarbonylalkylthio, or represents the —O—$R^6$ group, where
    $R^6$ represents an optionally halogen-substituted radical from the series comprising alkyl, alkenyl, alkinyl, alkoxyalkyl, alkylthioalkyl, alkylsulphinylalkyl, alkylsulphonylalkyl, aryloxyalkyl, arylthioalkyl, arylalkoxyalkyl, arylalkylthioalkyl, trialkylsilylalkyl, alkoxycarbonylalkyl, alkylaminocarbonylalkyl, arylaminocarbonylalkyl, N-alkyl-N-aryl-aminocarbonylalkyl, aralkyl, azolylalkyl or alkylideneamino, or represents an ammonium, alkylammonium, alkali metal or alkaline earth metal equivalent, or represents the

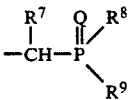

group, where
  $R^7$ represents hydrogen, alkyl, aryl, furyl, thienyl or pyridyl,
  $R^8$ represents alkyl or alkoxy,
  $R^9$ represents alkoxy and
  Q represents oxygen or sulphur,
or
  $R^6$ furthermore represents the —$(CH_2)_n$—$R^{10}$ group, where
    $R^{10}$ represents an optionally halogen-and/or alkyl-substituted heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl, and
    n represents the numbers 0, 1 or 2,
have now been found.

Furthermore, it has been found that the new (hetero)aryloxynaphthalene derivatives of the general formula (I) are obtained when (a) (hetero)aryloxynaphthylamines of the general formula (II)

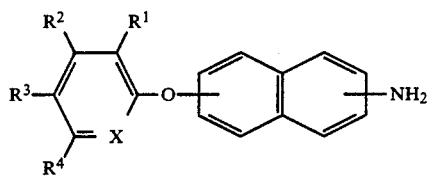

in which
$R^1$, $R^2$, $R^3$, $R^4$ and X have the abovementioned meanings,
or acid adducts of compounds of the formula (II) are reacted with sodium nitrite or potassium nitrite and with a hydrogen halide ($HX^1$) in the presence of water and if appropriate in the presence of an organic solvent, and the diazonium salts which are formed in this process, of the general formula (III)

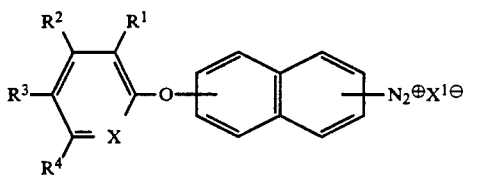

in which
$R^1$, $R^2$, $R^3$, $R^4$ and X have the abovementioned meanings and
$X^1$ represents halogen,
are reacted with acrylic acid derivatives of the general formula (IV)

$$Y^1—Z^2 \quad (IV)$$

in which $Y^1$ represents optionally branched and/or optionally halogen-substituted alkenyl and $Z^2$ represents cyano, carboxyl or alkoxycarbonyl, in the presence of hydrogen halides ($HX^1$), if appropriate in the presence of catalysts and if appropriate in the presence of water and the organic solvent which, if appropriate, has been used in the preparation of the compounds of the formula (III), and, if appropriate, the formation of other derivatives is carried out on the resulting compounds of the formula (I) by customary methods within the scope predetermined by the above definition of substituents, or (b) in the event that Y in formula (I) represents optionally branched alkanediyl and $R^1$, $R^2$, $R^3$, $R^4$, X and Z have the abovementioned meanings, when compounds of the formula (I) in which Y represents optionally branched alkanediyl which is at least monosubstituted by halogen, or represents optionally halogen- substituted alkenediyl, and $R^1$, $R^2$, $R^3$, $R^4$, X and Z have the abovementioned meanings, are reacted with hydrogen in the presence of a hydrogenation catalyst and in the presence of a diluent, or (c) in the event that Y in formula (I) represents halogen-substituted alkanediyl and $R^1$, $R^2$, $R^3$, $R^4$, X and Z have the abovementioned meanings, when compounds of the formula (I) in which Y represents alkanediyl or alkenediyl and $R^1$, $R^2$, $R^3$, $R^4$, X and Z have the abovementioned meanings, are reacted with halogenating agents, if appropriate in the presence of catalysts and if appropriate in the presence of diluents, or (d) in the event that Z in formula (I) represents the —CO—$Z^1$ group, where $Z^1$ represents hydroxy, and $R^1$, $R^2$, $R^3$, $R^4$, X and Y have the abovementioned meanings, when compounds of the formula (I) in which Z represents cyano or the —CO—$Z^1$ group, where $Z^1$ represents methoxy or ethoxy, and $R^1$, $R^2$, $R^3$, $R^4$, X and Y have the meanings specified above, are reacted with water, if appropriate in the presence of a hydrolysis auxiliary and if appropriate in the presence of an organic solvent, or (e) in the event that Z in formula (I) represents the —CO—$Z^1$ group, where $Z^1$ represents halogen, and $R^1$, $R^2$, $R^3$, $R^4$, X and Y have the abovementioned meanings, when compounds of the formula (I) in which Z represents the —CO—$Z^1$ group, where $Z^1$ represents hydroxyl, and $R^1$, $R^2$, $R^3$, $R^4$, X and $Z^1$ have the abovementioned meanings, are reacted with a halogenating agent, if appropriate in the presence of a catalyst and if appropriate in the presence of a diluent, or (f) in the event that $Z^1$ in formula (I) represents the —CO—$Z^1$ group, where $Z^1$ has the abovementioned meaning with the exception of halogen, and $R^1$, $R^2$, $R^3$, $R^4$, X and Y have the abovementioned meanings, when compounds of the formula (I) in which $Z^1$ represents the —CO—$Z^1$ group, where $Z^1$ represents halogen, and $R^1$, $R^2$, $R^3$, $R^4$, X and Y have the abovementioned meanings, are reacted with compounds of the general formula (V)

$$H—Z^1 \qquad (V)$$

in which $Z^1$ has the abovementioned meaning with the exception of halogen, if appropriate in the presence of an acid acceptor and if appropriate in the presence of a diluent, or (g) in the event that Y in formula (I) represents optionally branched and/or optionally halogen-substituted alkenediyl, and $R^1$, $R^2$, $R^3$, $R^4$, X and Z have the abovementioned meanings, when compounds of the formula (I) in which Y represents alkanediyl which has at least 2 carbon atoms and which is at least monosubstituted by halogen, and $R^1$, $R^2$, $R^3$, $R^4$, X and $Z^1$ have the abovementioned meanings, are reacted with bases, if appropriate in the presence of diluents.

Finally, it has been found that the new (hetero)aryloxynaphthalene derivatives of the general formula (I) have excellent herbicidal properties.

Surprisingly, the (hetero)aryloxynaphthalene derivatives of the formula (I) according to the invention have a considerably more powerful effect against weeds than methyl α-[4-(2,4-dichloro-phenoxy)-phenoxy]-propionate, which is a previously known active compound of a similar structure and the same direction of action.

The carbon chains in the radicals such as, for example, alkyl, alkenyl, alkoxy, alkylsulphonyl or alkoxycarbonyl, are in each case straight-chain or branched.

The invention preferably relates to compounds of the formula (I) in which $R^1$ represents hydrogen, fluorine, chlorine, bromine, cyano or trifluoromethyl, $R^2$ represents hydrogen, fluorine or chlorine, $R^3$ represents fluorine, chlorine, bromine, trifluoromethyl, trifluoromethoxy, trifluoromethylthio or trifluoromethylsulphonyl, $R^4$ represents hydrogen, fluorine or chlorine, X represents nitrogen or the C—$R^5$ group, where $R^5$ represents hydrogen, fluorine, chlorine or bromine, Y represents in each case optionally branched and/or optionally fluorine-, chlorine- and/or bromine-substituted alkanediyl or alkenediyl, in each case having 2 to 4 carbon atoms, and Z represents cyano or the —CO—$Z^1$ group, where $Z^1$ represents chlorine, hydroxyl, amino, $C_1$–$C_6$-alkylamino, $C_3$–$C_4$-alkenylamino, $C_3$–$C_4$-alkinylamino, phenylamino, benzylamino, $C_3$–$C_4$-alkoxycarbonyl-$C_1$–$C_2$-alkylamino, cyanoamino, di-($C_1$–$C_4$-alkyl)-amino, di-($C_3$–$C_4$-alkenyl)-amino, $C_1$–$C_4$-alkylsulphonylamino, phenylsulphonylamino, tolylsulphonylamino, hydroxyamino, $C_1$–$C_6$-alkoxyamino, hydrazino, $C_1$–$C_4$-alkylsulphonylhydrazino, phenylsulphonylhydrazino, tolylsulphonylhydrazino, $C_1$–$C_4$-alkylthio, phenylthio, benzylthio or $C_1$–$C_4$-alkoxy-carbonyl-$C_1$–$C_2$-alkylthio, or represents the —O—$R^6$ group, where $R^6$ represents an optionally fluorine- and/or chlorine-substituted radical from the series comprising $C_1$–$C_6$-alkyl, $C_3$–$C_4$-alkenyl, $C_3$–$C_4$-alkinyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulphinyl-$C_1$–$C_4$-alkyl, $C_1$–$C_3$-alkylsulphonyl-$C_1$–$C_4$-alkyl, phenoxy-$C_1$–$C_3$-alkyl, trimethylsilylmethyl, phenylthio-$C_1$–$C_3$-alkyl, benzyloxy-$C_1$–$C_3$-alkyl, benzylthio-$C_1$–$C_3$-alkyl, $C_1$–$C_4$-alkoxy-carbonyl-$C_1$–$C_2$-alkyl, $C_1$–$C_4$-alkylamino-carbonyl-$C_1$–$C_2$-alkyl, phenylaminocarbonyl-$C_1$–$C_4$-alkyl, N-($C_1$–$C_4$-alkyl)-N-phenyl-aminocarbonyl-$C_1$–$C_4$-alkyl, benzyl, pyrazolyl-$C_1$–$C_4$-alkyl or $C_2$–$C_4$-alkylideneamino, or represents an ammonium, a $C_1$–$C_4$-alkylammonium, a sodium, potassium or calcium equivalent, or represents the

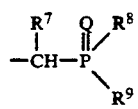

group
where
R[7] represents hydrogen, $C_1$–$C_4$-alkyl, phenyl, furyl, thienyl or pyridyl,
R[8] represents $C_1$–$C_4$-alkyl or $C_1$–$C_4$-alkoxy,
R[9] represents $C_1$–$C_4$-alkoxy and
Q represents oxygen or sulphur,
or
R[6] furthermore represents the —(CH$_2$)$_n$—R[10] group, where
n represents the numbers 0, 1 or 2 and
R[10] represents an optionally fluorine-, chlorine-, bromine- and/or $C_1$–$C_4$-alkyl-substituted heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl.

In particular, the invention relates to compounds of the formula (I) in which
R[1] represents cyano, fluorine or chlorine,
R[2] represents hydrogen, fluorine or chlorine,
R[3] represents chlorine or trifluoromethyl,
R[4] represents hydrogen, fluorine or chlorine,
X represents nitrogen or the C—R[5] group, where
R[5] represents hydrogen, fluorine or chlorine,
Y represents in each case optionally chlorine- and/or bromine-substituted ethane-1,2-diyl, propane-1,2-diyl, ethene-1,2-diyl or propene-1,2-diyl and
Z represents cyano or the —CO—Z[1] group, where
Z[1] represents chlorine, hydroxyl, amino, $C_1$–$C_4$-alkylamino, phenylamino, $C_1$–$C_4$-alkoxy-carbonyl-$C_1$–$C_2$-alkylamino, di-($C_1$–$C_3$-alkyl)-amino, diallylamino, $C_1$–$C_4$-alkylsulphonylamino, phenylsulphonylamino, hydroxyamino, cyanoamino, $C_1$–$C_4$-alkoxyamino, hydrazino, $C_1$–$C_4$-alkylsulphonylhydrazino, phenylsulphonylhydrazino, $C_1$–$C_4$-alkylthio or $C_1$–$C_4$-alkoxy-carbonyl-$C_1$–$C_2$-alkylthio, or represents the group —O—R[6], where
R[6] represents $C_1$–$C_4$-alkyl, $C_1$–$C_2$-alkoxy-$C_1$–$C_2$-alkyl, $C_1$–$C_2$-alkylthio-$C_1$–$C_2$-alkyl, $C_1$–$C_2$-alkylsulphinyl-$C_1$–$C_2$-alkyl, $C_1$–$C_2$-alkylsulphonyl-$C_1$–$C_2$-alkyl, benzyloxy-$C_1$–$C_3$-alkyl, benzylthio-$C_1$–$C_3$-alkyl, $C_1$–$C_4$-alkoxycarbonyl-$C_1$–$C_2$-alkyl, $C_1$–$C_4$-alkylaminocarbonyl-$C_1$–$C_2$-alkyl, benzyl or trimethylsilylmethyl, or represents an ammonium, $C_1$–$C_3$-alkylammonium, sodium, or potassium equivalent, or represents the

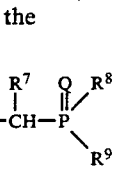

group, where

R[7] represents hydrogen, methyl, phenyl, furyl, thienyl or pyridyl,
R[8] represents methoxy or ethoxy,
R[9] represents methoxy or ethoxy and
Q represents oxygen or sulphur
or
R[6] furthermore represents the (—CH$_2$—)$_n$R[10] group, where
n represents the numbers 0, 1 or 2 and
R[10] represents an optionally chlorine-and/or methyl-substituted heterocyclic radical from the series comprising furyl, tetrahydrofuryl, thienyl, perhydropyranyl, oxazolyl, thiazolyl and dioxolanyl.

Very particularly preferred groups of compounds of the formula (I) are those of the formulae (IA) to (IE) below, in which R[1], R[2], R[3], R[4], X, Y and Z in each case have the meanings indicated above as being particularly preferred.

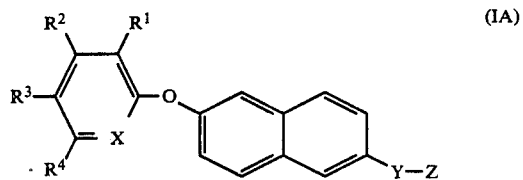
(IA)

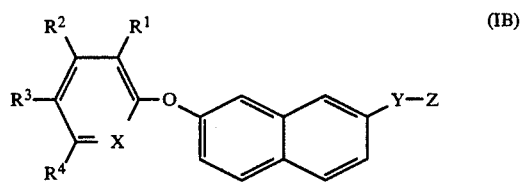
(IB)

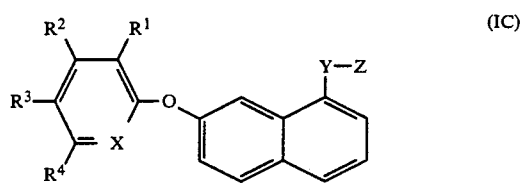
(IC)

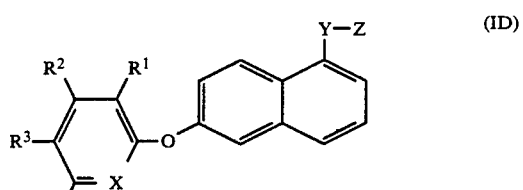
(ID)

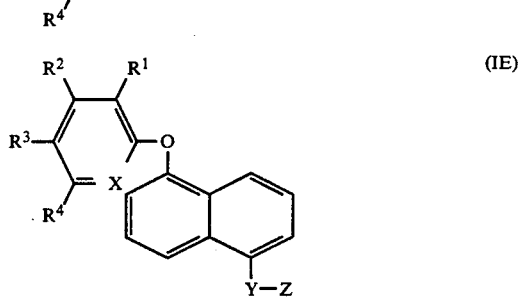
(IE)

Particularly preferred compounds of the formula (I) are those in which
R[1] represents chlorine,
R[2] represents hydrogen,
R[3] represents trifluoromethyl, $R^4$ represents hydrogen, X represents nitrogen or the $C-R^5$ group, where
$R^5$ represents fluorine or chlorine, Y represents in each case chlorine- and/or bromine-substituted ethane-1,2-diyl, propane-1,2-diyl, ethene-1,2-diyl or propene-1,2-diyl, and Z represents the $-CO-Z^1$ group, where
$Z^1$ represents $C_1-C_4$-alkoxy, in particular methoxy.

Particularly preferred from amongst these are the groups of compounds of the formula (IB) and (IE).

The compounds of the formula (I) listed in Table 1 below are mentioned by way of example:

TABLE 1

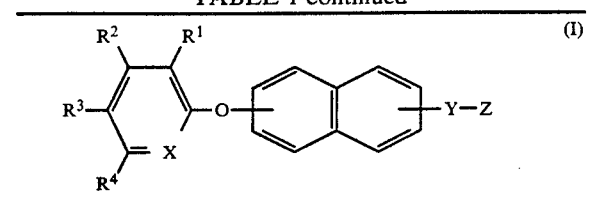

| $R^1$ | $R^2$ | $R^3$ | $R^4$ | X | Y | Z |
|---|---|---|---|---|---|---|
| Cl | H | Cl | H | CH | $-CH_2-CHCl-$ | $COOCH_3$ |
| Cl | H | Cl | H | N | $-CH_2-CHCl-$ | $COOC_2H_5$ |
| Cl | H | $CF_3$ | H | CH | $-CH_2-CHCl-$ | $COOCH_3$ |
| Cl | H | $CF_3$ | H | CH | $-CH_2-CHBr-$ | $COOC_2H_5$ |
| Cl | H | $CF_3$ | H | CH | $-CH(CH_3)-CHCl-$ | $COOCH_3$ |
| Cl | H | $CF_3$ | H | N | $-CH_2-CHCl-$ | $COOC_2H_5$ |
| Cl | H | $CF_3$ | H | CH | $-CH=CH-$ | $COOC_2H_5$ |
| Cl | H | $CF_3$ | H | C-Cl | $-CH_2-CHCl-$ | $COOCH_3$ |
| Cl | H | $CF_3$ | H | C-F | $-CH_2-CHCl-$ | $COOC_2H_5$ |
| Cl | H | $CF_3$ | H | C-F | $-CH=CH-$ | $COOC_2H_5$ |
| Cl | H | $CF_3$ | H | N | $-CH=CH-$ | $COOCH_3$ |
| Cl | H | $CF_3$ | H | C-Cl | $-C(CH_3)=CH-$ | $COOCH_3$ |
| Cl | H | $CF_3$ | H | C-Cl | $-CH=C(CH_3)-$ | $COOCH_3$ |
| Cl | H | $CF_3$ | F | C-F | $-CHBr-CH_2-$ | $COOCH_3$ |
| Cl | H | $CF_3$ | H | C-F | $-C(Br)=CH-$ | COOH |
| Cl | H | $SO_2CF_3$ | H | C-Cl | $-CH=CH-$ | COOH |
| Cl | H | $SO_2CF_3$ | H | CH | $-CH_2-CHCl-$ | $COOC_2H_5$ |
| Cl | H | $CF_3$ | H | CH | $-CH_2-C(Cl)(CH_3)-$ | $COOCH_3$ |
| Cl | H | $CF_3$ | H | CH | $-CH(CH_3)-CHCl-$ | COOH |
| Cl | H | $CF_3$ | H | C-F | $-CH(Br)-CH_2-$ | COOH |
| Cl | H | $CF_3$ | H | C-F | $-C(CH_3)(Br)-CH_2-$ | COOH |
| Cl | H | $CF_3$ | H | C-F | $-C(Br)_2-CH_2-$ | COOH |
| Cl | H | $CF_3$ | H | C-Cl | $-CH_2-CHCl-$ | COOH |
| Cl | H | $CF_3$ | H | N | $-CH_2-CHCl-$ | COOH |
| Cl | H | $SO_2CF_3$ | H | C-Cl | $-CH_2-CHCl-$ | COOH |
| Cl | H | $CF_3$ | Cl | C-Cl | $-CH=CH-$ | COOH |
| Cl | H | Cl | H | CH | $-CH_2-CH_2-$ | $COOCH_3$ |
| Cl | H | Cl | H | N | $-CH_2-CH_2-$ | $COOC_2H_5$ |
| Cl | H | Cl | H | CH | $-CH=CH-$ | $COOC_2H_5$ |
| Cl | H | $CF_3$ | H | CH | $-CH_2-CH_2-$ | $COOC_2H_5$ |
| Cl | H | $CF_3$ | H | N | $-CH_2-CH_2-$ | $COOC_4H_9$ |
| Cl | H | $CF_3$ | H | CH | $-CH_2-CH(CH_3)-$ | $COOCH_3$ |
| Cl | H | $CF_3$ | H | CH | $-CH=CH-$ | $COOC_2H_5$ |
| Cl | H | $CF_3$ | H | CH | $-CH=C(CH_3)-$ | $COOCH_3$ |
| Cl | H | $CF_3$ | H | C-Cl | $-CH_2-CH_2-$ | $COOCH_3$ |
| Cl | H | $CF_3$ | H | C-Cl | $-CH=CH-$ | COOH |
| Cl | H | $CF_3$ | H | C-F | $-CH_2-CH_2-$ | $COOC_2H_5$ |
| Cl | H | $CF_3$ | H | C-F | $-CH=CH-$ | $COOC_2H_5$ |
| Cl | H | $CF_3$ | H | N | $-CH=CH-$ | $COOC_2H_5$ |
| Cl | H | $SO_2CF_3$ | H | CH | $-CH_2-CH_2-$ | $COOCH_3$ |
| Cl | H | $SO_2CF_3$ | H | CH | $-CH=CH-$ | COOH |
| Cl | H | $SO_2CF_3$ | H | C-Cl | $-CH_2-CH_2-$ | COOH |
| Cl | H | $SO_2CF_3$ | H | C-Cl | $-CH=CH-$ | $COOC_2H_5$ |
| Cl | H | $CF_3$ | Cl | C-Cl | $-CH_2-CH_2-$ | COOH |
| Cl | H | $CF_3$ | F | C-Cl | $-CH=CH-$ | $COOCH_3$ |
| Cl | H | $CF_3$ | F | C-F | $-CH=CH-$ | COOH |
| Cl | H | $CF_3$ | Cl | C-Cl | $-CH=CH-$ | $COOCH_3$ |

TABLE 1-continued

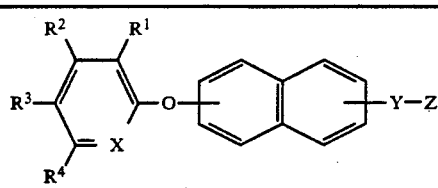

| R¹ | R² | R³ | R⁴ | X | Y | Z |
|---|---|---|---|---|---|---|
| F | H | CF₃ | H | C—F | —CH₂—CH₂— | COOCH₃ |
| Cl | H | CF₃ | H | C—Cl | —CH₂—CH(CH₃)— | COOH |
| Cl | H | CF₃ | H | C—Cl | —CH=CH— | COCl |
| Cl | H | CF₃ | H | C—Cl | —CH(CH₃)—CH₂— | COCH₃ |
| Cl | H | Cl | H | CH | —CH₂—CH₂— | CN |
| Cl | H | Cl | H | N | —CH₂—CH₂— | CN |
| Cl | H | Cl | H | N | —CH=CH— | CN |
| Cl | H | CF₃ | H | CH | —CH₂—CH₂— | CN |
| Cl | H | CF₃ | H | CH | —CH₂—CH(Cl)— | CN |
| Cl | H | CF₃ | H | CH | —CH=CH— | CN |
| Cl | H | CF₃ | H | N | —CH₂—CH₂— | CN |
| Cl | H | CF₃ | H | C—Cl | —CH₂—CH₂— | CN |
| Cl | H | CF₃ | H | C—Cl | —CH₂—CH(CH₃)— | CN |
| Cl | H | CF₃ | H | C—Cl | —CH₂—CH(Cl)— | CN |
| Cl | H | CF₃ | H | C—Cl | —CH=CH— | CN |
| Cl | H | CF₃ | H | C—F | —CH₂—CH₂— | CN |
| Cl | H | CF₃ | H | C—F | —CH=CH— | CN |
| Cl | H | CF₃ | H | C—F | —CH₂—CH(Cl)— | CN |
| Cl | H | CF₃ | H | C—Cl | —CH(Br)—CH₂— | CN |
| Cl | H | CF₃ | H | C—F | —CH(Br)—CH₂— | CN |
| Cl | H | CF₃ | Cl | C—Cl | —CH₂—CH₂— | CN |
| Cl | H | CF₃ | F | C—Cl | —CH=CH— | CN |
| Cl | H | SO₂CF₃ | H | CH | —CH₂—CH(Cl)— | CN |
| Cl | H | SO₂CF₃ | H | C—Cl | —CH₂—CH₂— | CN |
| Cl | H | CF₃ | H | CH | —CH=C(CH₃)— | CN |
| Cl | H | CF₃ | H | C—Cl | —CH(CH₃)—CH₂— | CN |
| Cl | H | Cl | H | CH | —CH₂—CH₂— | —CO—Cl |
| Cl | H | Cl | H | N | —CH₂—CH₂— | —CO—Cl |
| Cl | H | CF₃ | H | CH | —CH₂—CH₂— | —CO—Cl |

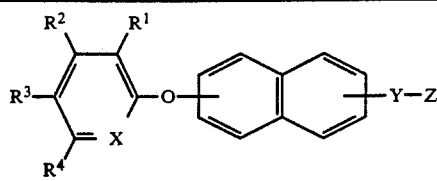

| R¹ | R² | R³ | R⁴ | X | Y | Z |
|---|---|---|---|---|---|---|
| Cl | H | CF₃ | H | CH | —CH₂—CH(Cl)— | —CO—Cl |
| Cl | H | CF₃ | H | CH | —CH=CH— | —CO—Cl |
| Cl | H | CF₃ | H | CH | —CH₂—CH(Br)— | —CO—Cl |
| Cl | H | CF₃ | H | CH | —CH₂—CH(CH₃)— | —CO—Cl |
| Cl | H | CF₃ | H | CH | —CH(Br)—CH₂— | —CO—Cl |
| Cl | H | CF₃ | H | N | —CH₂—CH₂— | —CO—Cl |
| Cl | H | CF₃ | H | C—Cl | —CH₂—CH₂— | —CO—Cl |
| Cl | H | CF₃ | H | C—Cl | —CH₂—CH(Cl)— | —CO—Cl |
| Cl | H | CF₃ | H | C—Cl | —CH=CH— | —CO—Cl |
| Cl | H | CF₃ | H | C—F | —CH₂—CH₂— | —CO—Cl |
| Cl | H | CF₃ | H | C—F | —CH₂—CH(Cl)— | —CO—Cl |
| Cl | H | CF₃ | H | C—F | —CH=CH— | —CO—Cl |
| Cl | H | CF₃ | Cl | C—Cl | —CH₂—CH₂— | —CO—Cl |
| Cl | H | CF₃ | F | C—Cl | —CH=CH— | —CO—Cl |
| Cl | H | SO₂CF₃ | H | CH | —CH₂—CH₂— | —CO—Cl |
| Cl | H | SO₂CF₃ | H | C—Cl | —CH₂—CH₂— | —CO—Cl |
| Cl | H | CF₃ | H | C—Cl | —CH(CH₃)—CH₂— | —CO—Cl |
| Cl | H | Cl | H | CH | —CH₂—CH(Cl)— | COOCH₃ |
| Cl | H | Cl | H | N | —CH₂—CH(Cl)— | COOC₂H₅ |
| Cl | H | CF₃ | H | CN | —CH₂—CH(Cl)— | CN |
| Cl | H | CF₃ | H | CH | —CH(Br)—CH₂— | COOCH₃ |
| Cl | H | CF₃ | H | N | —CH₂—CH(Cl)— | COOC₂H₅ |
| Cl | H | CF₃ | H | C—Cl | —CH₂—CH(Cl)— | COOCH₃ |
| Cl | H | CF₃ | H | CH | —CH(CH₃)—CH(Cl)— | CN |

TABLE 1-continued (I)

$$\text{structure with } R^1, R^2, R^3, R^4, X, \text{ naphthyl-O-, Y-Z}$$

| $R^1$ | $R^2$ | $R^3$ | $R^4$ | X | Y | Z |
|---|---|---|---|---|---|---|
| Cl | H | Cl | H | CH | —CH$_2$—CH(Cl)— | COOCH$_3$ |
| Cl | H | Cl | H | N | —CH$_2$—CH(Cl)— | COOC$_2$H$_5$ |
| Cl | H | CF$_3$ | H | CN | —CH$_2$—CH(Cl)— | CN |
| Cl | H | CF$_3$ | H | CH | —CH(Br)—CH$_2$— | COOCH$_3$ |
| Cl | H | CF$_3$ | H | N | —CH$_2$—CH(Cl)— | COOC$_2$H$_5$ |
| Cl | H | CF$_3$ | H | C—Cl | —CH$_2$—CH(Cl)— | COOCH$_3$ |
| Cl | H | CF$_3$ | H | CH | —CH(CH$_3$)—CH(Cl)— | CN |

The examples indicated in Table 1 are applied specifically to each group of compounds of the formula (I) which are outlined by the formulae (IA), (IB), (IC), (ID) and (IE).

If, for example, 6—(2,6-dichloro-4-trifluoromethyl-phenoxy)-2-naphthylamine, sodium nitrite and hydrochloric acid, and subsequently methyl acrylate, are used as starting substances for process (a) according to the invention, the course of the reaction can be represented by the following equation:

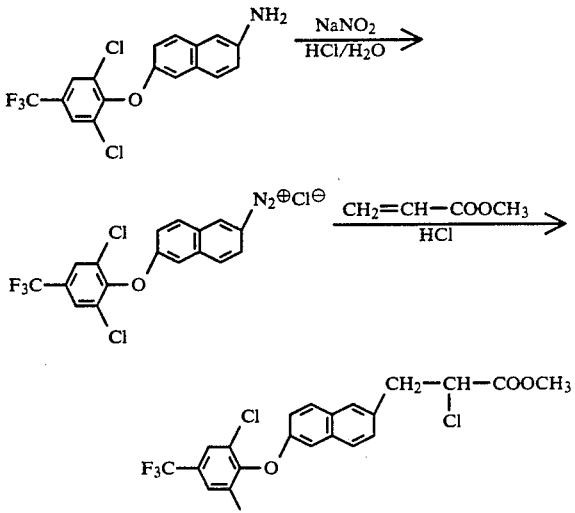

If ethyl 2-chloro-3-[7—(3,5-dichloro-pyridin-2-yl-oxy)-naphthalen-2-yl]-propionate is used as the starting substance and Raney nickel as the catalyst in process (b) according to the invention, the course of the reaction can be represented by the following equation:

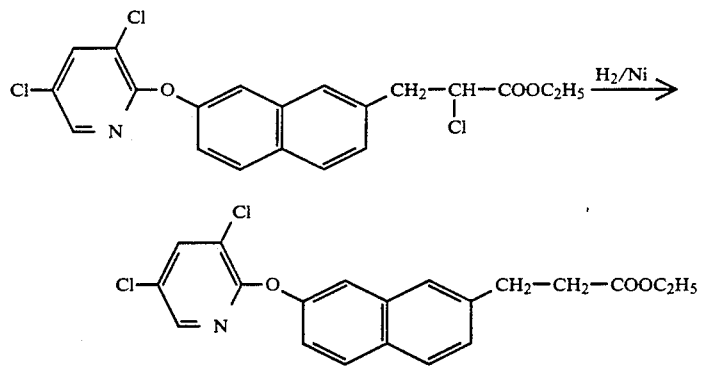

If butyl 3-[5-(2-fluoro-4-trifluoromethyl-phenoxy)naphthalen-1-yl]-propionate and N-bromo-succinimide are used as starting substances in process (c) according to the invention, the course of the reaction can be represented by the following equation:

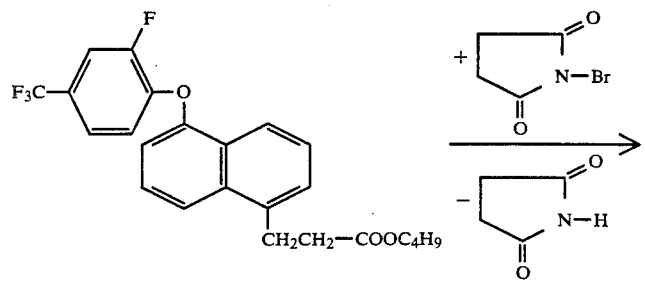

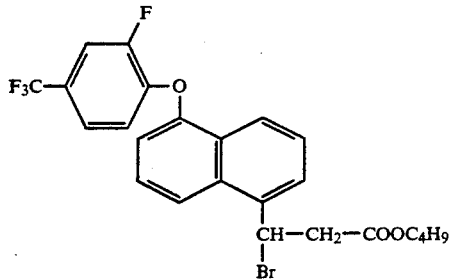

If 3-[7-(2-chloro-6-fluoro-4-trifluoromethyl-phenoxy)-naphthalen-1-yl]-propionitrile and sodium hydroxide solution are used as starting substances in process (d) according to the invention, the course of the reaction can be represented by the following equation:

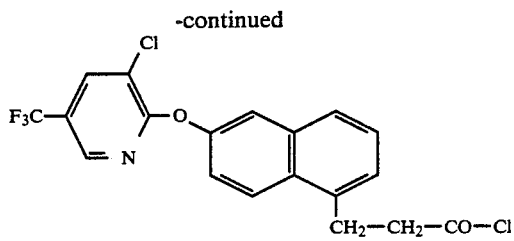

If 3-[(7-(2-chloro-6-fluoro-4-trifluoromethyl-phenoxy)-naphthalen-2-yl]-propionyl chloride and 2-ethoxyethanol are used as starting substances in process (f) according to the invention, the course of the reaction can be represented by the following equation:

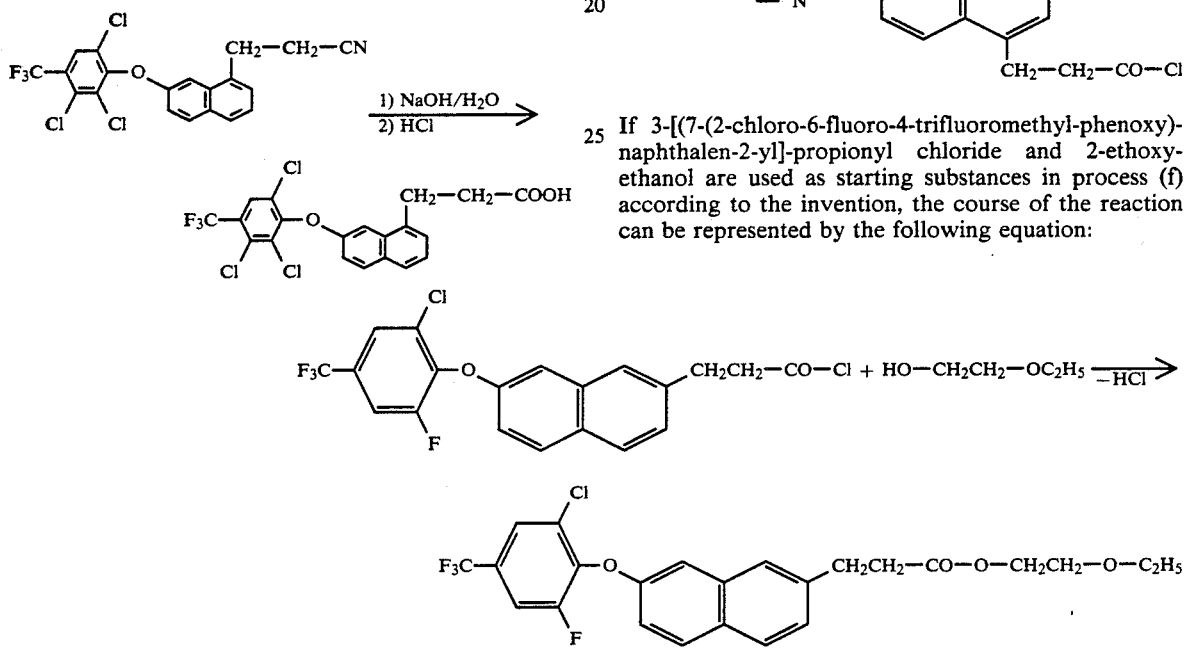

If ethyl 2-chloro-3-[6—(2-chloro-4-trifluoromethyl-phenoxy)-naphthalen-2-yl]-propionate and triethylamine are used as starting substances in process (g) according to the invention, the course of the reaction can be represented by the following equation:

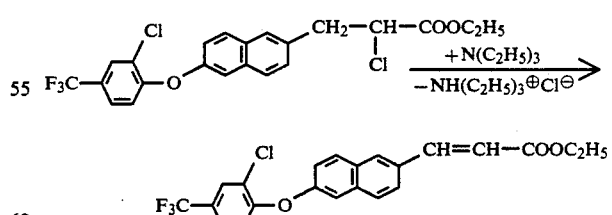

If 3-[6-(3-chloro-5-trifluoromethyl-pyridin-2-yl-oxy)-naphthalen-1-yl]-propionic acid and thionyl chloride are used as starting substances in process (e) according to the invention, the course of the reaction can be represented by the following equation:

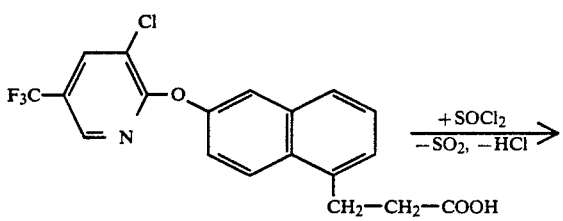

Formula (II) provides a general definition of the (hetero)aryloxynaphthylamines to be used as starting substances in process (a) according to the invention for the preparation of compounds of the formula (I).

In formula (II), $R^1$, $R^2$, $R^3$, $R^4$ and X preferably, or in particular, have those meanings which have already been indicated above in connection with the description of the compounds of the formula (I) according to the invention as being preferred, or particularly preferred, for $R^1$, $R^2$, $R^3$, $R^4$ and X.

Examples of the starting substances of the formula (II) are listed in Table 2 below.

TABLE 2

Examples of the starting substances of the formula (II)

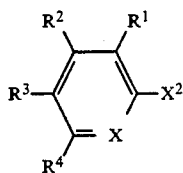

(II)

| $R^1$ | $R^2$ | $R^3$ | $R^4$ | X |
|---|---|---|---|---|
| Cl | H | Cl | H | CH |
| Cl | H | Cl | H | N |
| Cl | H | CF$_3$ | H | CH |
| Cl | H | CF$_3$ | H | N |
| Cl | H | CF$_3$ | H | C—Cl |
| Cl | H | CF$_3$ | H | C—F |
| Cl | H | CF$_3$ | F | C—Cl |
| Cl | H | CF$_3$ | Cl | C—Cl |
| CN | H | CF$_3$ | H | CH |
| Cl | H | SO$_2$CF$_3$ | H | CH |
| Cl | H | SO$_2$CF$_3$ | H | C—Cl |
| F | H | CF$_3$ | H | C—F |

The examples indicated in Table 2 are specifically true in each case for all the starting substances of the formula (II) which correspond to the abovementioned isomer groups (IA), (IB), (IC), (ID) and (IE).

Starting substances of the formula (II) were hitherto unknown from the literature. The new (hetero)aryloxynaphthylamines of the formula (II) are obtained when halogeno(hetero)aryl compounds of the general formula (VI)

(VI)

in which
$R^1$, $R^2$, $R^3$, $R^4$ and X have the abovementioned meanings and
$X^2$ represents fluorine or chlorine,
are reacted with hydroxynaphthylamines of the general formula (VII)

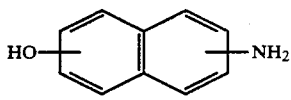

(VII)

or with their hydrogen halides
in the presence of an acid acceptor, such as, for example, sodium hydroxide or potassium hydroxide, and in the presence of a diluent, such as, for example, dimethylformamide, dimethylacetamide, dimethyl sulphoxide, tetramethylene sulphone or N-methyl-pyrrolidone, at temperatures between 20° C. and 150° C., and the reaction products are worked up by customary methods.

Formula (VI) provides a general definition of the halogeno(hetero)aryl compounds required as starting substances. In formula (VI), $R^1$, $R^2$, $R^3$, $R^4$ and X preferably, or in particular, have those meanings which have already been mentioned in connection with the description of the compounds of the formula (I) according to the invention as being preferred, or particularly preferred, for $R^1$, $R^2$, $R^3$, $R^4$ and X.

Examples of the halogeno-(hetero)aryl compounds of the formula (VI) which may be mentioned are: 4-chloro-benzotrifluoride, 3,4-dichloro-benzotrifluoride, 3,4,5-trichloro-benzotrifluoride, 3,4-dichloro-5-fluorobenzotrifluoride, 2,3,4,5-tetrachloro-benzotrifluoride, 3,5-dichloro-2,4-difluoro-benzotrifluoride, 3-chloro-4,5-difluoro-benzotrifluoride, and also 2,3,5-trichloropyridine and 2,3-dichloro-5-trifluoromethyl-pyridine.

The compounds of the formula (VI) are known and/or can be prepared by processes known per se (cf. J. Chem. Soc. 1969, 211–217; loc. cit. 1971, 1547–1549; EP-A 34,402; U.S. Pat. No. 4,424,396; EP-A 145,314; FR TM A 2,538,380 (Chem. Abstracts 102 (1985), 61914x)).

Examples which may be mentioned, of the hydroxynaphthylamines of the formula (VII) which are furthermore required as starting substances, are: 5-hydroxy-1-naphthylamine, 6-hydroxy-1-naphthylamine, 7-hydroxy-1-naphthylamine, 6-hydroxy-2-naphthylamine and 7-hydroxy-2-naphthylamine, as well as their hydrochlorides.

The compounds of the formula (VII) are known chemicals for organic synthesis.

Formula (IV) provides a general definition of the acrylic acid derivatives furthermore to be used as starting substances in process (a) according to the invention.
In formula (IV),
$Y^1$ preferably represents optionally branched and/or optionally fluorine-, chlorine- and/or bromine-substituted alkenyl having 2 to 4 carbon atoms and
$Z^2$ preferably represents cyano, carboxyl or $C_1$–$C_4$-alkoxy-carbonyl.
In formula (IV),
$Y^1$ in particular represents optionally chlorine- and/or bromine-substituted ethenyl or propenyl and
$Z^2$ in particular represents cyano, carboxyl, methoxycarbonyl or ethoxycarbonyl.

Examples of the starting substances of the formula (IV) which may be mentioned are: methyl acrylate, ethyl acrylate, methyl crotonate, ethyl crotonate, methyl 2-chloro-acrylate, ethyl 2-chloroacrylate, methyl 2-bromo-acrylate, ethyl 2-bromo-acrylate, methyl methacrylate, ethyl methacrylate, acrylonitrile, methacrylonitrile and 2-chloroacrylonitrile.

The compounds of the formula (IV) are known chemicals for organic synthesis.

Process (a) is carried out using a hydrogen halide (HX$^1$). Examples of hydrogen halides which may be mentioned are hydrogen fluoride, hydrogen chloride, hydrogen bromide and hydrogen iodide. Hydrogen chloride is preferably employed.

Process (a) is preferably carried out using an organic solvent. Particularly suitable solvents are ethers, such as, for example, glycol dimethyl ether and diglycol dimethyl ether, tetrahydrofuran and dioxane, ketones, such as, for example, acetone and methyl ethyl ketone, and also amides, such as, for example, dimethylformamide.

Furthermore, process (a) is preferably carried out in the presence of catalysts. Possible catalysts are, in particular, copper and copper compounds, such as, for example, copper(I) chloride, copper(II) chloride, copper(I) bromide, copper(I) iodide, copper(II) sulphate and copper(II) nitrate.

When carrying out process (a) according to the invention, the reaction temperatures can be varied within a relatively wide range. In general, the process is carried out at temperatures between $-20°$ C. and $+80°$ C., preferably at temperatures between $0°$ C. and $60°$ C.

Process (a) is generally carried out under atmospheric pressure.

For carrying out process (a) according to the invention, between 0.8 and 2.5 mols, preferably between 1.1 and 2.0 mols, of sodium nitrite or potassium nitrite, between 2 and 50 mols, preferably between 5 and 25 mols, of hydrogen halide, and between 1 and 3 mols, preferably between 1.2 and 2.5 mols, of acrylic acid derivative of the formula (IV) are generally employed per mol of (hetero)aryloxynaphthylamine of the formula (II).

Process (a) can be carried out under the customary conditions of the "Meerwein arylation". In a preferred embodiment of process (a), the first step is to stir the starting compound of the formula (II) in a diluent which contains at least water and one hydrogen halide, and to diazotize the compound using an aqueous solution of sodium nitrite or potassium nitrite, with cooling. The acrylic acid derivative of the formula (IV) and if appropriate the catalyst is then added to the reaction mixture. As soon as the evolution of nitrogen has subsided—if appropriate after slightly heating the product can be worked up by customary methods.

For example, the reaction mixture is diluted with an organic solvent which is virtually immiscible with water, such as, for example, diethyl ether or methylene chloride, and shaken, and the organic phase is separated off, washed with aqueous sodium hydrogen carbonate solution and with water, dried and filtered. The crude product of the formula (I), which is obtained as a residue after the filtrate has been concentrated, can be purified in a customary manner, for example by column chromatography.

With the proviso that Y represents alkanediyl which is optionally branched and at least monosubstituted by halogen or alkenediyl which is optionally branched and optionally substituted by halogen, formula (I) provides a general definition of the compounds to be used as starting substances in process (b) according to the invention. In this event, $R^1$, $R^2$, $R^3$, $R^4$, X and Z preferably, or in particular, have those meanings which have already been mentioned above within the scope of the description of the compounds of the formula (I) according to the invention as being preferred, or particularly preferred, for $R^1$, $R^2$, $R^3$, $R^4$, X and Z, and Y preferably represents in each case optionally branched, fluorine-, chlorine- and/or bromine-substituted alkanediyl or fluorine-, chlorine- and/or bromine-substituted alkenediyl, each having 2 to 4 carbon atoms, in particular represents chlorine- or bromine-substituted ethane-1,2-diyl, propane-1,2-diyl, ethene-1,2-diyl or propene-1,2-diyl.

The above-described starting substances of the formula (I) for process (b) are new compounds according to the invention; they can be prepared by processes (a) (c), (d), (e), (f) or (g) according to the invention.

Process (b) is carried out using a hydrogenation catalyst. Examples of suitable catalysts which may be mentioned are Raney nickel, platinum and palladium. It is preferred to employ Raney nickel as the catalyst in process (b).

Process (b) is carried out in the presence of a diluent. Diluents which are preferably employed in process (b) are hydrocarbons, such as cyclohexane, methylcyclohexane, benzene, toluene, xylene or cumene, alcohols, such as methanol, ethanol, propanol or isopropanol, ethers, such as glycol dimethyl ether, diglycol dimethyl ether, tetrahydrofuran or dioxane, or esters, such as methyl acetate or ethyl acetate, and also mixtures of the solvents mentioned.

When carrying out process (b) according to the invention, the reaction temperatures can be varied within a relatively wide range. In general, the process is carried out at temperatures between $0°$ C. and $150°$ C., preferably at temperatures between $20°$ C. and $100°$ C.

Process (b) is generally carried out under atmospheric pressure or elevated pressure up to about 200 bar, preferably up to about 100 bar.

Process (b) can be carried out under the conditions which are customary for catalytic hydrogenations. In a preferred embodiment of process (b), the starting compound of the formula (I) is mixed with the diluent and the catalyst, and hydrogen is then metered in until the consumption of hydrogen has ceased. When the hydrogenation is complete, the reaction mixture is filtered and the filtrate is concentrated, and the crude product is then obtained as a residue which can be purified in a customary manner, for example by column chromatography.

With the proviso that Y represents alkanediyl or alkenediyl, formula (I) provides a general definition of the compounds to be used as starting substances in process (c) according to the invention. In this event, $R^1$, $R^2$, $R^3$, $R^4$, X and $Z^1$ preferably, or in particular, have those meanings which have already been indicated above within the scope of the description of the compounds of the formula (I) according to the invention as being preferred, or particularly preferred, for $R^1$, $R^2$, $R^3$, $R^4$, X and Z, and Y preferably represents in each case optionally branched alkanediyl or alkenediyl, each having 2 to 4 carbon atoms, in particular represents ethane-1,2-diyl, propane-1,2-diyl, ethene-1,2-diyl or propene-1,2-diyl.

The above-described starting substances of the formula (I) for process (c) are new compounds according to the invention; they can be prepared by processes (b), (d), (e), (f) or (g) according to the invention.

Process (c) according to the invention is carried out using halogenating agents. Suitable halogenating agents are those which can be used for the halogenation of arylalkanes or of alkenes. Examples of preferred halogenating agents which may be mentioned are bromine, chlorine as well as N-bromo-succinimide and N-chlorosuccinimide.

If appropriate, process (c) is carried out in the presence of a catalyst. Suitable catalysts for this process are substances which form free radicals, such as, for example, 2,2'-azoisobutyric acid dinitrile (azoisobutyronitrile).

If appropriate, process (c) is carried out using diluents. Suitable diluents besides water are preferably relatively inert organic solvents, such as, for example, methylene chloride, chloroform, tetrachloromethane, chlorobenzene, o-dichlorobenzene and acetic acid. The diluent employed for the reaction with N-bromo- or N-chloro-succinimide is, in particular, tetrachloromethane.

When carrying out process (c) according to the invention, the reaction temperatures can be varied within a relatively wide range. In general, the process is carried out at temperatures between 0° C. and 150° C., preferably at temperatures between 20° C. and 100° C.

Process (c) according to the invention is generally carried out under atmospheric pressure. However, it is also possible to carry out the process under elevated or reduced pressure.

For carrying out process (c) according to the invention, the starting substances required in each case are generally employed in approximately equimolar amounts. However, it is also possible to use one of the two components employed in each case in a relatively large excess. In general, the reactions are carried out in a suitable diluent, and the reaction mixture is stirred for several hours at the specific temperature required. Working-up in process (c) according to the invention is carried out in each case by customary methods.

With the proviso that Z represents cyano or the $-CO-Z^1$ group, where $Z^1$ represents methoxy or ethoxy, formula (I) provides a general definition of the compounds to be used as starting substances in process (d) according to the invention. In this event, $R^1$, $R^2$, $R^3$, $R^4$, X and Y preferably, or in particular, have those meanings which have already been indicated above within the scope of the description of the compounds of the formula (I) according to the invention as being preferred, or particularly preferred, for $R^1$, $R^2$, $R^3$, $R^4$, X and Z, and Y.

The above-described starting substances of the formula (I) for process (d) are new compounds according to the invention; they can be prepared by processes (a), (b), (c), (f) or (g) according to the invention.

Process (d) according to the invention is preferably carried out in the presence of a hydrolysis auxiliary. Suitable hydrolysis auxiliaries are, in particular, strong acids, such as, for example, hydrochloric acid or sulphuric acid, or alkali metal hydroxides, such as, for example, sodium hydroxide or potassium hydroxide.

Process (d) is carried out in the presence of water and if appropriate in the presence of an organic solvent. Organic solvents which are employed are preferably alcohols, such as, for example, methanol or ethanol.

When carrying out process (d) according to the invention, the reaction temperatures can be varied within a relatively wide range. In general, the process is carried out at temperatures between 10° C. and 150° C., preferably at temperatures between 20° C. and 100° C.

Process (d) according to the invention is generally carried out under atmospheric pressure. However, it is also possible to carry out the process under elevated or reduced pressure.

For carrying out process (d), between 0.1 and 10 mols, preferably between 0.5 and 2 mols, of hydrolysis auxiliary are generally employed per mol of starting compound of the formula (VI). The reactants are generally combined at room temperature, and the reaction mixture is stirred until the reaction is complete, if appropriate at elevated temperature. If appropriate, the mixture is concentrated, cooled and acidified, and the reaction product is obtained in the form of crystals and can be isolated by filtering off with suction.

With the proviso that Z represents the $-CO-Z^1$ group, where $Z^1$ represents hydroxyl, formula (I) provides a general definition of the compounds to be used as starting substances in process (e) according to the invention. In this event, $R^1$, $R^2$, $R^3$, $R^4$, X and Y preferably, or in particular, have those meanings which have already been described above within the scope of the description of the compounds of the formula (I) according to the invention as being preferred, or particularly preferred, for $R^1$, $R^2$, $R^3$, $R^4$, X and Y.

The above-described starting substances of the formula (I) for process (e) are new compounds according to the invention; they can be prepared by processes (a), (b), (c), (d) or (g) according to the invention.

Process (e) according to the invention is carried out using a halogenating agent. Agents which can be employed are those customary for the reaction of carboxylic acids to carboxylic acid halides.

Examples for this process which may be mentioned are phosgene, thionyl chloride, phosphoryl chloride and benzotrichloride. It is preferred to use thionyl chloride as the halogenating agent.

If appropriate, process (e) is carried out in the presence of a catalyst. Catalysts which can be used are those customary for the preparation of acid chlorides from acids, such as, for example, pyridine or dimethylformamide.

If appropriate, process (e) is carried out in the presence of a diluent. Diluents which are preferably suitable are inert organic solvents from the series of the halogenated hydrocarbons, such as, for example, methylene chloride, chloroform, tetrachloromethane or 1,2-dichloroethane.

When carrying out process (e) according to the invention, the reaction temperatures can be varied within a relatively wide range. In general, the process is carried out at temperatures between 0° C. and 100° C., preferably at temperatures between 10° C. and 90° C.

Process (e) is generally carried out under atmospheric pressure.

For carrying out process (e), between 1 and 100 mols, preferably between 2 and 50 mols, of halogenating agent are generally employed per mol of starting compound of the formula (I). The reactants are generally combined at room temperature and the reaction mixture is stirred until the reaction is complete, if required at elevated temperature. The reaction product which remains after the volatile components have been distilled off under reduced pressure, can be purified by recrystallization or can be employed for subsequent reactions without further purification.

With the proviso that Z represents the $-CO-Z^1$ group, where $Z^1$ represents halogen, formula (I) provides a general definition of the compounds to be used as starting substances in process (f) according to the invention. In this event, $R^1$, $R^2$, $R^3$, $R^4$, X and Y preferably, or in particular, have those meanings which have already been mentioned above within the scope of the description of the compounds of the formula (I) according to the invention as being preferred, or particularly preferred, for $R^1$, $R^2$, $R^3$, $R^4$, X and Y, and $Z^1$ preferably represents fluorine, chlorine or bromine, in particular chlorine.

The above-described starting substances of the formula (I) for process (f) are new compounds according to the invention; they can be prepared by process (e) according to the invention.

In the compounds of the general formula (V), which are to be employed as other starting substances for process (f), $Z^1$ preferably, or in particular, has the meaning which has already been mentioned above within the scope of the description of the compounds of the formula (I) according to the invention as being preferred, or particularly preferred, for $Z^1$, halogen being excepted.

Examples which may be mentioned of the compounds of the formula (V) are: methylamine, ethylamine, propylamine, isopropylamine, cyanoamide, dimethylamine, diethylamine, hydroxylamine, O-methylhydroxylamine, hydrazine, methylsulphonylhydrazin, methanol, ethanol, propanol, isopropanol, butanol, isobutarol, sec-butanol, 2-methoxy-ethanol, 2-ethoxyethanol, 2-methylthio-ethanol, 2-ethylthioethanol, 2-benzyloxy-ethanol, 2-benzylthio-ethanol, diethyl hydroxymethanephosphonate and dimethyl hydroxymethanephosphonate, dimethyl 1-hydroxy-ethanephosphonate and diethyl 1-hydroxy-ethanephosphonate, dimethyl 1-hydroxy-1-phenyl-methanephosphonate and diethyl 1-hydroxy-1-phenyl-methanephosphonate, 3-hydroxyfuran, furfuryl alcohol, perhydrofurfuryl alcohol, methyl lactate and ethyl lactate, and methyl glycolate and ethyl glycolate.

These compounds are known chemicals for synthesis.

Process (f) according to the invention is preferably carried out using diluents. Possible diluents for this process are virtually all inert organic solvents.

These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (f) according to the invention are all acid-binding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate and potassium carbonate, sodium tertbutoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO), are preferably suitable.

When carrying out process (f) according to the invention, the reaction temperatures can be varied within a relatively wide range. In general, the process is carried out at temperatures between 0° C. and 100° C., preferably at temperatures between 10° C. and 50° C.

Process (f) according to the invention is generally carried out under atmospheric pressure. However, it is also possible to carry out the process under elevated or reduced pressure.

For carrying out process (f) according to the invention, the starting substances required in each case are generally employed in approximately equimolar amounts. However, it is also possible to use one of the two components employed in each case in a relatively large excess. The reactions are generally carried out in a suitable diluent in the presence of an acid acceptor, and the reaction mixture is stirred for several hours at the specific temperature required.

Working-up in process (f) according to the invention is carried out in each case by customary methods. For example, the reaction mixture is diluted with water—if appropriate after concentrating—and the desired reaction product is extracted using an organic solvent which is virtually immiscible with water, for example methylene chloride, chloroform, diethyl ether, toluene or xylene. The organic extraction solution is washed with water, dried using a customary drying agent, such as, for example, sodium sulphate, and filtered.

After the filtrate has been concentrated, the compounds of the formula (I) are obtained as crude products, which can be purified in a customary manner, for example by chromatography and/or by recrystallization.

With the proviso that Y represents alkanediyl which has at least 2 carbon atoms and is at least monosubstituted by halogen, formula (I) provides a general definition of the compounds to be used as starting substances in process (g) according to the invention. In this event, $R^1$, $R^2$, $R^3$, $R^4$, X and $Z^1$ preferably, or in particular, have those meanings which have already been indicated above within the scope of the description of the compounds of the formula (I) according to the invention as being preferred, or particularly preferred, for $R^1$, $R^2$, $R^3$, $R^4$, X and Z, and Y preferably represents optionally branched alkanediyl which has 2 to 4 carbon atoms and is monosubstituted or disubstituted by fluorine, chlorine and/or bromine, in particular represents ethane-1,2-diyl or propane-1,2-diyl, in each case monosubstituted by chlorine or bromine.

The above-described starting substances of the formula (I) for process (g) are new compounds according to the invention; they can be prepared by processes (a), (c), (d) or (f) according to the invention.

Process (g) according to the invention is carried out using bases. It is preferred to employ the bases which are customarily used for eliminating hydrogen halides.

These include, in particular, alkali metal hydroxides, such as sodium hydroxide and potassium hydroxide, alkali metal alkoxides, such as sodium ethoxide, potassium ethoxide, sodium tert-butoxide and potassium tert-butoxide, as well as certain amines, such as triethylamine, tripropylamine, tributylamine, ethyldiisopropylamine, ethyldicyclohexylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

Process (g) is preferably carried out using diluents. Suitable diluents for this process are virtually all inert organic solvents. These preferably include alcohols, such as methanol, ethanol, propanol, isopropanol, butanol, isobutanol, sec-butanol and tert-butanol, and also ether alcohols, such as 2-methoxy-ethanol, 2-ethoxy-ethanol and triethylene glycol, ethers, such as diisopropyl ether, diisobutyl ether, tetrahydrofuran and dioxane, furthermore dimethylformamide, dimethylacetamide, N-methylpyrrolidone, dimethyl sulphoxide and tetramethylene sulphone.

When carrying out process (g) according to the invention, the reaction temperatures can be varied within a relatively wide range. In general, the process is carried out at temperatures between 0° C. and 250° C., preferably at temperatures between 50° C. and 200° C.

Process (g) according to the invention is generally carried out under atmospheric pressure. However, it is also possible to carry out the process under elevated or reduced pressure.

For carrying out process (g) according to the invention, between 1 and 3 mols, preferably between 1.2 and 2.5 mols, of a base are generally employed per mol of starting compound of the formula (I). The reactants are generally combined at room temperature, and the reaction mixture is then stirred until the reaction is complete, generally at elevated temperature. Working-up is carried out by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds in monocotyledon crops, especially using the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also e used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used as mixtures with known herbicides for controlling weeds, finished formulations o tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl- 1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4 TM methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropy-1)-3,4-dimethyl-2,6-dinitroaniline (PENDIMETHALIN); O-(6-chloro-3-phenyl-pyridazin-4-yl) S-octylthiocarbonate (PYRIDATE); 4-ethylamino-2-t-butylamino-6-methylthio-s-triazine (TERBUTRYNE) and methyl 3-[[[[(4-methoxy-6-methyl-1,3,5-triazin-2-yl)-amino]-carbonyl]-amino]sulphonyl]-thiophene-2-carboxylate (THLAMETURON). Surprisingly, some mixtures also show synergistic action.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules.

They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

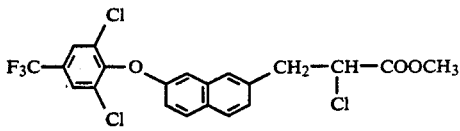

Process (a)

14.6 g (0.039 mol) of 7-(2,6-dichloro-4-trifluoromethylphenoxy)-2-aminonaphthalene are dissolved in 80 ml of acetone and 50 ml of conc. hydrochloric acid. While the mixture is cooled to 0°--5° C., 3 g (0.043 mol) of sodium nitrite, dissolved in 4 ml of water, are added dropwise in the course of 30 minutes. Stirring is continued for 5 minutes, and then 4.7 g (0.054 mol) of methyl acrylate are first added and after a further 40 minutes 0.6 g of copper(II) chloride, still with cooling. The reaction mixture is allowed to cool to room temperature overnight and is then poured into methylene chloride/water. The organic phase is evaporated, and the residue is chromatographed over silica gel using toluene/hexane (1:1).

2.2 g (12% of theory) of methyl 2-chloro-3-[7-(2,6-dichloro-4-trifluoromethyl-phenoxy)-naphthalen-2-yl]-propionate are obtained in the form of crystals of orange color and melting point 136° C.

Example 2

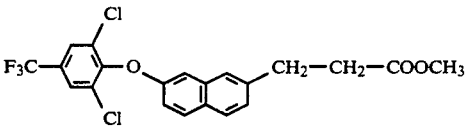

Process (b)

1.3 g (0.0025 mol) of methyl 2-chloro-3-[7-(2,6-dichloro-4-trifluoromethyl-phenoxy)-naphthalen-2-yl]-propionate are taken up in a mixture of 50 ml of methanol and 50 ml of toluene, 1.0 g of Raney nickel is added, and the mixture is then hydrogenated for 2 hours at 40° C. and 50 bar. The mixture is subsequently filtered, and the solvent is carefully removed from the filtrate by distillation under a waterpump vacuum.

0.5 g (45% of theory) of methyl 3-[7-(2,6-dichloro-4-trifluoromethyl-phenoxy)-naphthalen-2-yl]-propionate are obtained as an oily residue.

$^1$H-NMR (CDCl$_3$,δ): 2.65 (t) and 3.05 (t) (—CH$_2$—CH$_2$—COOCH$_3$)

The compounds of the formula (I), which are specified in greater detail by the "isomer groups" of the formulae (IA), (IB), (IC), (ID) and (IE) and which are listed in Table 3 below, can be obtained analogously to Examples 1 and 2 and following the general description of the preparation processes according to the invention.

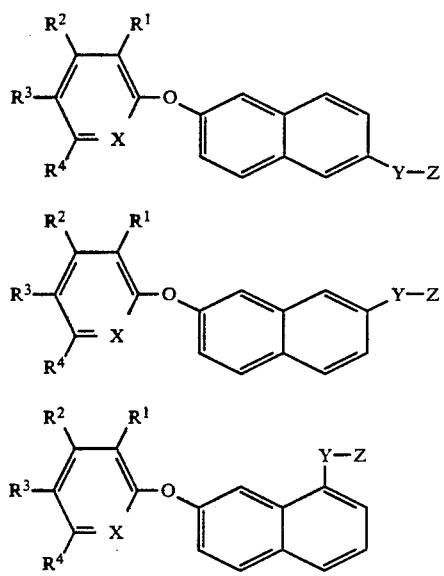

(IA)
(IB)
(IC)

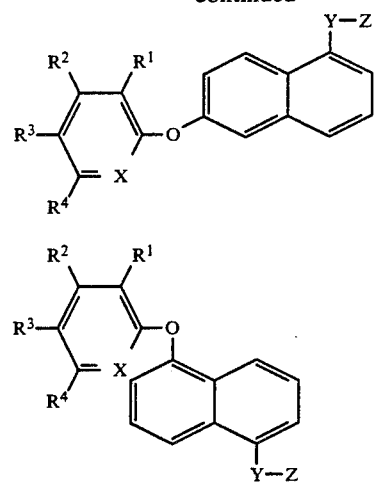

(ID)
(IE)

TABLE 3

Examples of compounds of the formula (1)

| Example No. | Isomer group | R¹ | R² | R³ | R⁴ | X | Y | Z | Physical data |
|---|---|---|---|---|---|---|---|---|---|
| 3 | IB | Cl | H | CF₃ | H | C—F | —CH₂—CH(Cl)— | COOCH₃ | δ: 4.53(t)(—CH(Cl)—) |
| 4 | IB | Cl | H | CF₃ | H | C—F | —CH₂—CH₂— | COOCH₃ | δ: 2.69 and 3.08 (—CH₂—CH₂—) |
| 5 | IB | Cl | H | CF₃ | H | C—Cl | —CH(CH₃)—CH(Cl)— | COOCH₃ | |
| 6 | IB | Cl | H | CF₃ | H | C—Cl | —CH(CH₃)—CH₂— | COOCH₃ | |
| 7 | IB | Cl | H | CF₃ | H | C—Cl | —CH₂—C(CH₃)(Cl)— | COOCH₃ | m.p. 133° C. |
| 8 | IB | Cl | H | CF₃ | H | C—Cl | —CH₂—CH(CH₃)— | COOCH₃ | m.p. 88° C. |
| 9 | IB | Cl | H | CF₃ | H | N | —CH₂—CH(Cl)— | COOCH₃ | δ: 4.53(t)(—CH(Cl)—) |
| 10 | IB | Cl | H | CF₃ | H | N | —CH₂—CH₂— | COOCH₃ | |
| 11 | IE | Cl | H | CF₃ | H | C—Cl | —CH₂—CH(Cl)— | COOCH₃ | δ: 4.66(t)(—CH(Cl)—) |
| 12 | IE | Cl | H | CF₃ | H | C—Cl | —CH₂—CH₂— | COOCH₃ | |
| 13 | IB | Cl | H | CF₃ | H | C—F | —CH(Br)—CH₂— | COOCH₃ | δ: 5.51(t)(—CH(Cl)—) |

STARTING SUBSTANCES OF THE FORMULA (II)

Example (II-1)

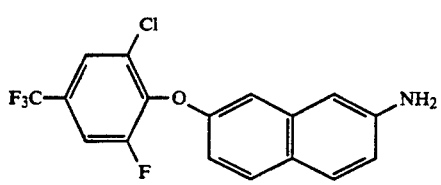

32.5 g (0.15 mol) of 3-chloro-4,5-difluoro-benzotrifluoride are added to a mixture, heated to 120° C., of 35.3 g (0.15 mol) of 7-hydroxy-2-naphthylamine hydrochloride, 20.1 g (0.36 mol) of potassium hydroxide (powder) and 300 ml of dimethyl sulphoxide, with stirring, and the reaction mixture is stirred at 120° C. for 20 hours. The mixture is then concentrated at 1 mbar, and the residue is dissolved in ethyl acetate, washed with water, dried with sodium sulphate and filtered. The solvent is carefully removed from the filtrate by distillation under a waterpump vacuum.

42.7 g (80% of theory) of 7-(2-chloro-6-fluoro-4-trifluoromethyl-phenoxy)-2-naphthylamine are obtained as an oily residue.

$^1$H-NMR (CDCl$_3$, δ): 6.85 (d), 6.95 (d), 7.60 (d).

The following are obtained analogously:

Example (II-2)

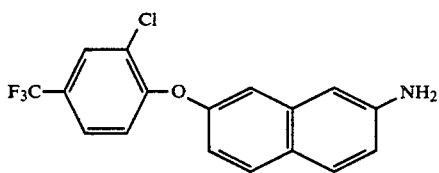

Melting point: 115° C.

Example (II-3)

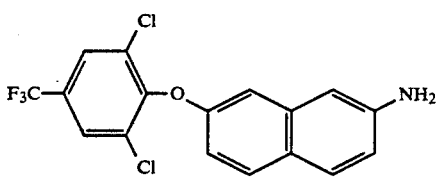

$^1$H-NMR (DMSO, δ): 8.15 (s)

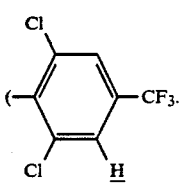

Example (II-4)

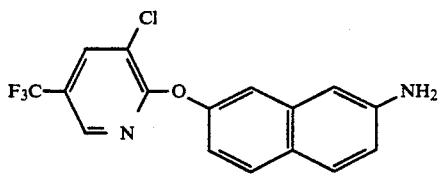

Melting point: 121° C.

USE EXAMPLES

In the Use Examples which follow, the compound listed below is used as comparison substance:

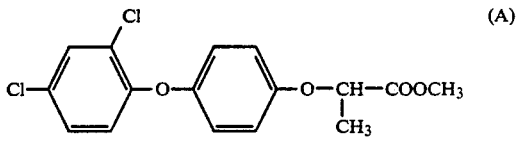
(A)

methyl α-[4-(2,4-dichloro-phenoxy)-phenoxy]-propionate (diclofop-methyl) (disclosed in DE-OS (German Published Specification) 2,223,894/Example 86).

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds of Preparation Examples (1), (2), (3), (7), (8) and (11) show a clearly superior activity compared with the comparison substance (A).

It will be understood that the specification and examples are illustrative but not limitative of the present invention and that other embodiments within the spirit and scope of the invention will suggest themselves to those skilled in the art.

We claim:

1. An aryloxynaphthalene derivative of the formula

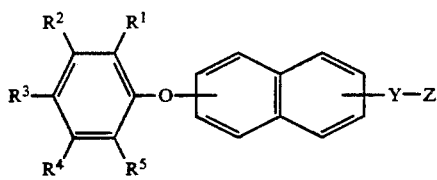

in which
R¹ represents hydrogen, halogen, or trifluoromethyl,
R² represents hydrogen or halogen,
R³ represents halogen, trifluoromethyl or trifluoromethoxy, or
R⁴ represents hydrogen or halogen,
R⁵ represents hydrogen or halogen,
Y represents in each case optionally branched and/or optionally halogen-substituted alkanediyl or alkenediyl, in each case having at least 2 carbon atoms, and
Z represents —CO—Z¹ group, where
Z¹ represents halogen, hydroxyl, or represents the —O—R⁶ group, where
R⁵ represents an optionally halogen-substituted radical from the group consisting of alkyl, alkenyl and alkinyl.

2. An aryloxynaphthalene derivative according to claim 1, in which
R¹ represents hydrogen, fluorine, chlorine, bromine or trifluoromethyl,
R² represents hydrogen, fluorine or chlorine,
R³ represents fluorine, chlorine, bromine, trifluoromethyl or trifluoromethoxy,
R⁴ represents hydrogen, fluorine or chlorine,
R⁵ represents hydrogen, fluorine, chlorine or bromine,
Y represents in each case optionally branched and/or optionally fluorine-, chlorine- and/or bromine-substituted alkanediyl or alkenediyl, in each case having 2 to 4 carbon atoms, and
Z represents —CO—Z¹ group, where
Z¹ represents chlorine, hydroxyl, or represents the —O—R⁶ group, where
R⁶ represents an optionally fluorine-and/or chlorine-substituted radical from the group consisting of $C_1$-$C_6$-alkyl, $C_3$-$C_4$-alkenyl and $C_3$-$C_4$-alkinyl.

3. An aryloxynaphthalene derivative according to claim 1, in which
R¹ represents cyano, fluorine or chlorine,
R² represents hydrogen, fluorine or chlorine,
R³ represents chlorine or trifluoromethyl,
R⁴ represents hydrogen, fluorine or chlorine,
R⁵ represents hydrogen, fluorine or chlorine,
Y represents in each case optionally chlorine- and/or bromine-substituted ethane-1,2-diyl, propane-1,2-diyl, ethene-1,2-diyl or propene-1,2-diyl and
Z¹ represents chlorine, hydroxyl, or represents the group —O—R⁶, where
R⁵ represents $C_1$-$C_4$-alkyl.

4. An aryloxynaphthalene derivative according to claim 1, in which
R¹ represents chlorine,
R² represents hydrogen,
R³ represents trifluoromethyl,
R⁴ represents hydrogen,
R⁵ represents fluorine or chlorine, Y represents in each case chlorine- and/or bromine-substituted ethane-1,2-diyl, propane-1,2-diyl, ethene-1,2-diyl or propene-1,2-diyl, and
Z¹ represents —CO—$C_1$—$C_4$-alkoxy.

5. A compound according to claim 1, wherein such compound is methyl 2-chloro-3-[7-(2,6-dichloro-4-trifluoromethylphenoxy)-naphthalen-2-yl]-propionate of the formula

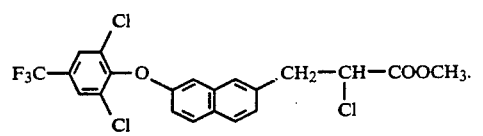

6. A compound according to claim 1, wherein such compound is methyl 3-[7-(2,6-dichloro-4-trifluoromethylphenoxy)-naphthalen-2-yl]-propionate of the formula

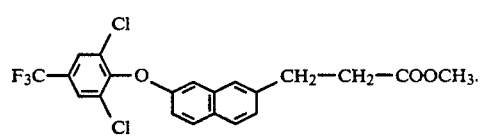

7. A compound according to claim 1, wherein such compound is methyl 2-chloro-3-[7-(2-chloro-6-fluoro-4-trifluoromethylphenoxy)-naphthalen-2-yl]-propionate of the formula

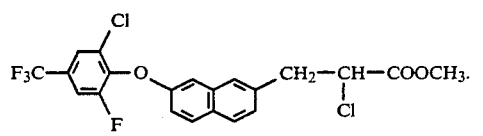

8. A compound according to claim 1, wherein such compound is methyl 2-chloro-2-methyl-3-[7-(2,6-dichloro-4-trifluoromethyl-phenoxy)-naphthalen-2-yl]-propionate of the formula

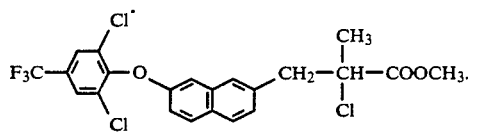

9. A compound according to claim 1, wherein such compound is methyl 2-methyl-3-[7-(2,6-dichloro-4-trifluoromethyl-phenoxy)naphthalen-2-yl]-propionate of the formula

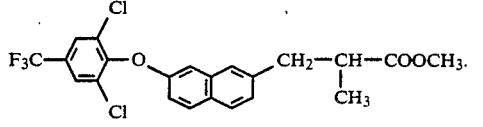

10. A compound according to claim 1, wherein such compound is methyl 2-chloro-3-[7-(2,6-dichloro-4-trifluoromethyl-phenoxy)-naphthalen-4-yl]-propionate of the formula

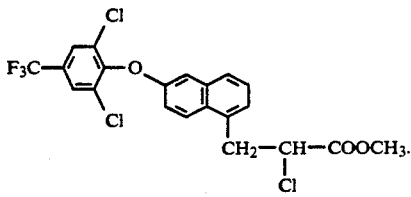

11. A herbicidal composition comprising a herbicidally effective amount of a compound according to claim 1 and a diluent.

12. A method of combating unwanted vegetation which comprises applying to such vegetation or to a locus from which it is desired to exclude such vegetation a herbicidally effective amount of a compound according to claim 1.

13. The method according to claim 12, wherein such compound is methyl 2-chloro-3-[7-(2,6-dichloro-4-trifluoromethyl-phenoxy)-naphthalen-2-yl]-propionate, methyl 3-[7-(2,6-dichloro-4-trifluoromethylphenoxy)-naphthalen-2-yl]-propionate, methyl 2-chloro-3-[7-(2-chloro-6-fluoro-4-trifluoromethyl-phenoxy)-naphthalen-2-yl]-propionate methyl 2-chloro-2-methyl-3-[7-(2,6-dichloro-4-trifluoromethyl-phenoxy)-naphthalen-2-yl]-propionate, methyl 2-methyl-3-[7-(2,6-dichloro-4-trifluoromethyl-phenoxy)-naphthalen-2-yl]-propionate, or methyl-2-chloro-3-[7-(2,6-dichloro-4-trifluoromethyl-phenoxy)-naphthalen-4-yl]-propionate.

14. An aryloxynaphthalene derivative according to claim 1, of the formula

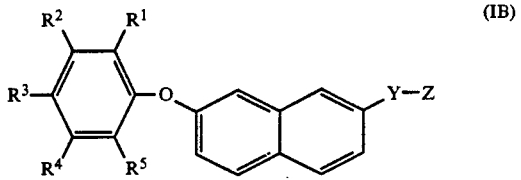

or

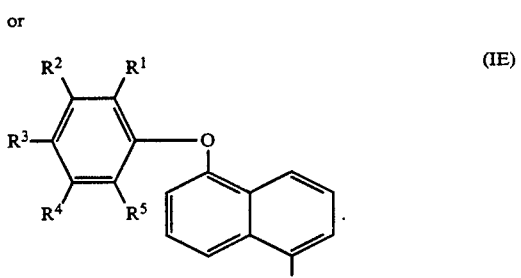

* * * * *

UNITED STATES PATENT AND TRADEMARK OFFICE
CERTIFICATE OF CORRECTION

PATENT NO. : 5,068,394

DATED : November 26, 1991

INVENTOR(S) : Andree et al.

It is certified that error appears in the above-identified patent and that said Letters Patent is hereby corrected as shown below:

Col. 31, line 14   After " fluoromethoxy " delete " or "

Col. 31, line 21   After " Z represents " insert -- the --

Col. 31, line 24   Delete " $R^5$ " and substitute -- $R^6$ --

Col. 31, line 42   Delete " Z represents $-CO-Z^1$ groupe, where "

Col. 31, line 61   Delete " $R^5$ " and substitute -- $R^6$ --

Col. 32, line 4    Delete " $Z^1$ " and substitute -- Z --

Signed and Sealed this

Sixth Day of July, 1993

Attest:

MICHAEL K. KIRK

*Attesting Officer*     *Acting Commissioner of Patents and Trademarks*